United States Patent [19]

Bolton

[11] Patent Number: 5,024,323
[45] Date of Patent: Jun. 18, 1991

[54] SUTURE EXTENDER AND NEEDLE GUARD

[76] Inventor: Bernard Bolton, 18444 Cornell, Southfield, Mich. 48075

[21] Appl. No.: 412,006

[22] Filed: Sep. 25, 1989

[51] Int. Cl.⁵ .................... A61B 17/06; B65D 83/10
[52] U.S. Cl. .................... 206/63.3; 206/365; 206/472; 606/228
[58] Field of Search .......... 606/228; 206/63.3, 363, 206/365, 491, 493, 495, 472, 433

[56] References Cited

U.S. PATENT DOCUMENTS

| 1,859,316 | 5/1932 | Sponsel | 206/365 |
| 3,301,393 | 1/1967 | Regan, Jr. et al. | 206/63.3 |
| 3,940,873 | 3/1976 | Lawless | 206/63.3 |
| 3,944,069 | 3/1976 | Eldridge, Jr. | 206/365 |
| 4,013,109 | 3/1977 | Sandel | 206/370 |
| 4,193,496 | 3/1980 | Barratt | 206/63.3 |
| 4,373,629 | 2/1983 | Ulin et al. | 206/370 |
| 4,596,329 | 6/1986 | Eldridge, Jr. | 206/63.3 |
| 4,869,364 | 9/1989 | Bray | 206/472 |

FOREIGN PATENT DOCUMENTS 2331638  6/1977  France .................. 206/63.3

Primary Examiner—Stephen C. Pellegrino
Assistant Examiner—Gary Jackson
Attorney, Agent, or Firm—Weintraub, DuRoss & Brady

[57] ABSTRACT

The needle guard protects medical personnel from accidental punctures associated with a surgical needle. The needle guard apparatus comprises two members, and a retainer. The surgical needle is securely retained between the two members when the retainer is in the engaged position. Preferably, when the retainer is in the engaged position, the surgical needle can only be removed from the needle guard by disengaging the retainer. After the sewing operation has been completed, the surgical needle and part of the suture extend outside of the two pieces of tissue. The surgical needle is then positioned within the needle guard, and the needle guard are securely engaged about the surgical needle. The portion of the suture extending between the needle guard and the tissue is used for knotting. The portion of the suture extending between the knot and the needle guard is cut, and the needle guard with the encased surgical needle is discarded of.

14 Claims, 1 Drawing Sheet

SUTURE EXTENDER AND NEEDLE GUARD

BACKGROUND OF THE INVENTION

1. Field of the Invention

The present invention relates to a suture extender and needle guard apparatus which protects a surgeon or seamstress from accidental punctures resulting from the use of a needle, and the method for using the needle guard apparatus, the needle guard apparatus being particularly useful in surgical applications.

2. Background Art

Surgical needles are commonly used for the stitching of body tissue during medical surgery, the needles being usually discarded after single use. The size and shape of the specific surgical needle design depends upon the particular body tissue involved and the purpose for the surgery.

Accidental needle punctures have been identified as a serious health hazard. All surgical needles are eventually disposed of after being use. If the patient has a communicable or infectious disease, the surgical needle is contaminated. Hence, the surgical needle must be carefully removed and disposed of to prevent contamination of attendant medical personnel.

The problem of disposing of contaminated surgical needles is particularly acute in treating patients afflicted with highly infectious diseases, such as acquired immune deficiency syndrome (AIDS), or hepatitis. For diseases such as AIDS, where the transmission mechanism is poorly understood, it is critical that all precautions be taken to protect personnel who come in contact with the afflicted patient.

Unfortunately, it is often not known which patients have been exposed to highly communicable diseases. Medical personnel are apprehensive of contamination, and by necessity assume that all patients are carriers. Accordingly, if the risk of contamination is not minimized, the quality of medical treatment available to all patients is compromised, while these highly communicable diseases spread through the community.

The disposal of contaminated surgical needles also poses a major health problem not only for hospitals, but for entire communities. When such supplies are merely discarded with other waste materials from the hospital, there is a risk that a contaminated surgical needle may subsequently puncture someone who comes in contact therewith, such as hospital cleaning personnel, garbage workers, or people at the municipal dump where the garbage is eventually received and destroyed.

What is needed is an apparatus, and a method for using the apparatus which will minimize the risk of puncture to surgeons and attendant medical personnel after the surgical needle has been pulled through the body tissue. The apparatus will preferably permanently retain the surgical needle therein, to protect other personnel who subsequently handle the discarded surgical needle.

SUMMARY OF THE INVENTION

The needle guard apparatus of the present invention provides a simple, safe, and convenient way of permanently encasing the needle not only minimizing the risk of contamination to surgeons who are responsible for manipulating the surgical needle and the suture during the completion of the surgery, but will also minimize the risk of all other personnel who may subsequently come into contact with the surgical needle.

Conventional surgical needles have a generally arcuate shape, and have a tissue-contact end and a suture-contact end. The suture-contact end is affixed to a suture, and a tip is disposed at the body-contact end.

The needle guard apparatus comprises two members, and means for retaining the two members together. One member is large enough to encase the entire surgical needle. The two members are preferably of a similar shape and rotatably attached, thereby enabling the two members to pivotally rotate toward and away from each other. The surgical needle may be securely retained between the two members when the retaining means is in an engaged position. The entire surgical needle is securely encased between the two members when the retaining means is in the engaged position. Preferably, when the retaining means is in the engaged position, the surgical needle can only be removed from the needle guard by disengaging the retaining means. Preferably, the two members each have a plurality of mating corrugated grooves disposed thereon for the secure retention of the suture (or thread) therebetween.

The needle guard is used after initially pulling the surgical needle and the suture through the tissue which is being sewn together. The surgical needle is then positioned within the needle guard, and the two members are securely engaged about the surgical needle. The needle guard encases the entire surgical needle, as a portion of the suture extends outside the needle guard and the tissue. The portion of the suture extending between the needle guard and the tissue is for the purpose of knotting. Preferably, the portion of the suture extending between the knot and the needle guard is then cut, and the needle guard with the surgical needle disposed therein is discarded.

For a more complete understanding of the suture extender and needle guard apparatus of the present invention, reference is made to the following detailed description and accompanying drawings in which the presently preferred embodiments of the invention are illustrated by way of example. As the invention may be embodied in several forms without departing from the spirit or essential characteristics thereof, it is expressly understood that the drawings are for purposes of illustration and description only, and are not intended as a definition of the limits of the invention. Throughout the following description and drawings, identical reference numbers refer to the same component throughout the several views.

DETAILED DESCRIPTION OF THE INVENTION

Figure 1:
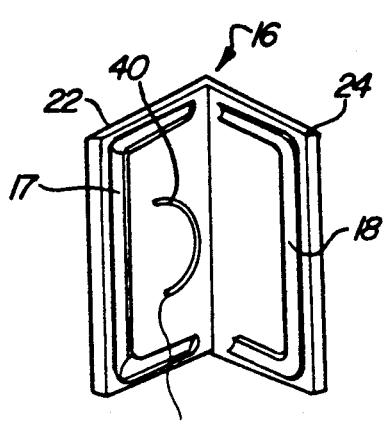
FIG. 1 is a perspective view of the preferred embodiment of the needle guard apparatus of the present invention in the disengaged position about a surgical needle and suture.
Figure 2:
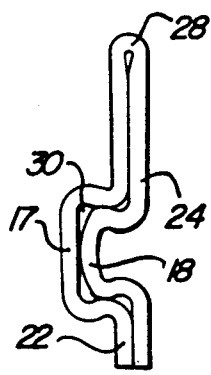
FIG. 2 depicts the retaining means of the needle guard apparatus of FIG. 1, as the protruding portion is retained within the recessed portion of one member when the needle guard is in the engaged position.

Referring now to the drawings, FIGS. 1 and 2 depict the preferred embodiment of the needle guard apparatus 16 of the present invention in the disengaged position about a surgical needle 40 and a suture 50. The surgical needle 40 is conventional having a generally arcuate shape, and a tissue-contact end 42 and a suture-contact end 44. The suture-contact end 44 is affixed to the suture 50, having a tip 46 disposed at the tissue-contact end 42.

The needle guard apparatus 16 comprises a first member 22 and a second member 24, and means 30 for retaining the first member 22 to the second member 24. The first member 22 is large enough to encase both the tissue-contact end 42 and the suture-contact end 44 of the surgical needle 40.

The retaining means 30 has both a disengaged position, and an engaged position. The surgical needle 40 may be securely retained between the first member 22 and the second member 24 when the retaining means 30 is in the engaged position. The retaining means 30 includes a recessed portion 17 disposed on the first member 22 and a protruding portion 18 disposed on the second member 24. The protruding portion 18 of the second member matingly engages into the recessed portion 17 of the first member (see FIG. 2), when the retaining means 30 is in the engaged position to securably retain the surgical needle 40 therebetween.

Preferably, the retaining means 30 is permanently retained in the engaged position, so that the surgical needle 40 can only be removed therefrom by the use of an elongated sharp tool (not shown). Hence, if the needle guard apparatus 16 is to incorporate this permanent retention feature the needle guard apparatus 16 must be initially packed and distributed in the disengaged position.

Preferably, when the retaining means 30 is in the engaged position, a pure tensile force applied to the portion of the suture 50 extending outside of the needle guard apparatus 16 will be insufficient to disengage the retaining means 30 or remove the surgical needle 40 from the needle guard apparatus 16, as the surgical needle 40 can only be removed from the needle guard apparatus 16 by disengaging the retaining means 30. Preferably, the first member 22 and the second member 24 each have a plurality of mating corrugated grooves 27 disposed thereon for the secure retention of the suture 50 therebetween. Preferably, the needle guard apparatus 16 is made of a rigid plastic material that is sterilizable, so that the needle guard apparatus 16 can be employed in a surgical environment.

Figure 3:
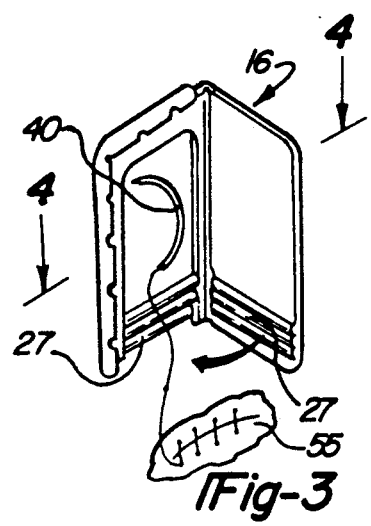
FIG. 3 is a perspective view of a second embodiment of the needle guard apparatus of the present invention in the disengaged position about a surgical needle and suture.
Figure 4:
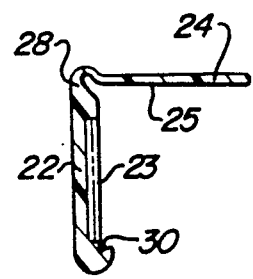
FIG. 4 is an enlarged cross-sectional view of Section 4—4 from FIG. 3, depicting the surgical needle disposed within one member of the needle guard apparatus, the needle guard apparatus being in the disengaged position.
Figure 5:
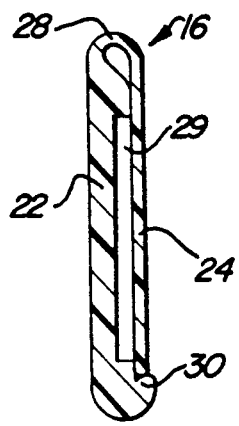
FIG. 5 is a cross-sectional view of the needle guard apparatus of FIG. 3 in the disengaged position.

FIGS. 3, 4, and 5 depict a second embodiment of the needle guard apparatus 16 of the present invention. The first member 22 and the second member 24 are preferably of a similar shape and are rotatably attached along a common hinge 28, thereby enabling the first member 22 to pivotally rotate toward and away from the second member 24. The inner surface 23 of the first member and the inner surface 25 of the second member 24 are preferably essentially planar.

Preferably, there is a recess 29 (see FIG. 5) between the first member 22 and the second member 24 in the engaged position so that the width of the surgical needle 40 does not interfere with the retaining means 30. Both the tissue-contact end 42 and the suture-contact end 44 of the surgical needle 40 are securely encased between the first member 22 and the second member 24 when the retaining means 30 is in the engaged position.

Figure 6:
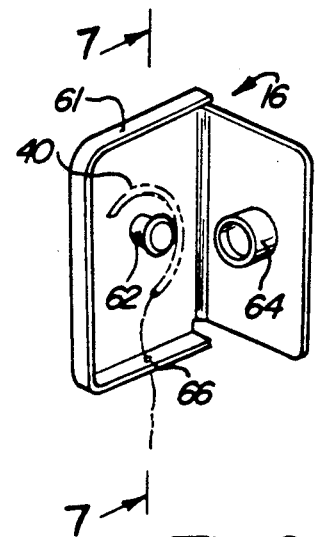
FIG. 6 is a perspective view of a third embodiment of the needle guard apparatus of the present invention, the needle guard apparatus being shown in the disengaged position, the surgical needle and the suture also being shown in phantom.
Figure 7:
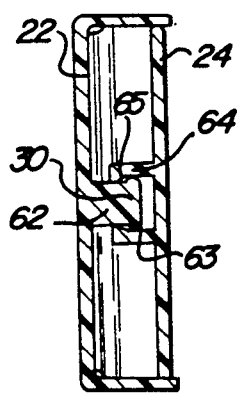
FIG. 7 is an enlarged cross-sectional view of the needle guard apparatus of FIG. 6 in the engaged position.

FIGS. 6 and 7 depict a third embodiment of the needle guard apparatus 16 of the present invention. The first member 22 has a flange 61 disposed about the perimeter thereof. A first protruding member 62 is disposed on the inner surface 23 of the first member 22, and a second protruding member 64 is disposed on the inner surface 25 of the second member 24. The first protruding member 62 and the second protruding member 64 are both generally cylindrical in shape, enabling the generally arcuate surgical needle 40 to be disposed thereabout prior to the engagement of the retaining means 30. The second protruding member 64 is hollow. The suture 50 fits through a slit 66 in the flange 61 first member 22 when the needle guard apparatus 16 is in the engaged position. The first protruding member 62 has an external flange 63 disposed on the outermost end thereof, and the second protruding member 64 has an internal flange 65 disposed on the outermost end thereof. The first protruding member 62 mates into the second protruding member 64, and is permanently retained therein when the retaining means 30 is engaged.

Figure 8:
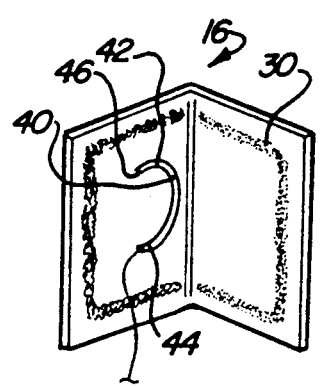
FIG. 8 is a perspective view of a fourth embodiment of the needle guard apparatus of the present invention, the needle guard apparatus being shown in the disengaged position.

FIG. 8 depicts a fourth embodiment of the needle guard apparatus 16 of the present invention. In this embodiment, Velcro ®, a hook and loop fastener or a sticky adhesive is disposed on the inner surface 25 of the second member 24, the Velcro ®, a hook and loop fastener, or the sticky adhesive serving as the retaining in the engaged position, the use of the Velcro ®, a hook and loop fastener, enables the needle guard apparatus 16 to also serve as a package prior to use.

If the needle guard apparatus 16 is of the design depicted in FIG. 8 (easy to reopen for repeated use), it can also be used as the packaging of the surgical needle 40 prior to use. Of course, if the needle guard apparatus 16 is also used for the packaging, either the needle guard apparatus 16 must be sterilized prior to use or the the surgical needle 40 must be encased within the needle guard apparatus 16 in a sterilized package. The needle guard apparatus 16 of the present invention also may be used in nonmedical applications. The needle guard apparatus 16 can be used in general sewing applications to retain a conventional sewing needle therebetween (not shown). Such a needle guard apparatus 16 must be generally easy to reopen for repeated use. The needle guard apparatus 16 can also be used as a needle extender during the knotting of the suture 50.

The needle guard apparatus 16 of the present invention is used in the manner hereinafter set forth. The surgical needle 40 and the affixed suture 50 are pulled through the tissue 55 which are being sewn together. The surgical needle 40 and part of the suture 50 extend outside of the tissue 55. The surgical needle 50 is positioned within the needle guard apparatus 16. The first member 22 and the second member 24 are securely engaged about the surgical needle 40. The needle guard apparatus 16 encases both the tissue-contact end 42 and the suture-contact end 44 of the surgical needle 40, as a portion of the suture 50 extends outside the needle guard apparatus 16 and the tissue 55. The portion of the suture 50 extending between the needle guard apparatus 16 and the tissue 55 is preferably tied into a knot. Preferably, the portion of the suture 50 extending between the knot and the needle guard apparatus 16 is subsequently cut, and the needle guard apparatus 16 with the encased surgical needle 40 disposed therein is discarded.

Also, the needle guard apparatus 16 may be used as a suture extender, wherein the suture 50 is positioned in the apparatus 16. The apparatus 16 can then be used to locate one end of the suture 50 and to extend the portion of the suture 50 outside of the tissue 55 being sewn together, to act as a suture extender during knotting.

While the suture extender and needle guard apparatus 16 has been described in conjunction with specific embodiments, it is evident that many alternatives, modifications, and variations will be apparent to those skilled in the art in light of the disclosure herein. It is intended that the metes and bounds of the invention be determined by the appended claims rather than by the language of the above specification, and that all such alternatives, modifications, and variations which form a functional or conjointly cooperative equivalent are intended to be included within the spirit and scope of these claims.

I claim:

1. A suture-extender apparatus for the secure retention of a needle-type device, the needle type device having two ends, one end of the needle-type device being affixable to a suture, the apparatus comprising:
    (a) a first member and a second member, the first member being large enough to encase both ends of the needle-type device, the first member and the second member each having an inner surface, the first and second member being sized and shaped to attain therewithin a surgical needle-type device;
    (b) means for retaining the second member to the first member when the needle-type device is disposed therebetween, the retaining means having an engaged position and a disengaged position, both ends of the needle-type device being securely encaseable between the first member and the second member when the retaining means is in the engaged position;
    the second member being permanently retainable with the first member when the retaining means is engaged; and wherein the suture-extender readily fits into a hand of a physician enabling the physician to complete a surgical procedure without exposure to puncture from the needle-type device.

2. The suture-extender apparatus of claim 1, wherein the first member and the second member form a snap-fit engagement when the retaining means is in the engaged position.

3. The suture-extender apparatus of claim 1, further comprising:
    a surgical needle having a generally arcuate shape, the surgical needle being securely retainable between the first and second member when the retaining means is in the engaged position, the surgical needle having a tissue-contact end and a suture end.

4. The suture-extender of claim 1, wherein the inner surface of the first member is essentially planar.

5. The suture-extender of claim 1, wherein the first and the second member each have a plurality of corrugated grooves disposed thereon for the secure retention of the suture, the corrugated grooves of the second member vesting within the corrugated grooves of the first member.

6. A needle guard apparatus comprising:
    (a) a surgical needle-type device, the surgical needle-type device having a generally arcuate shape, the surgical needle-type device having a tissue-contact end and suture-contact end, the surgical needle-type device having a tip disposed at the tissue-contact end;
    (b) a first member and a second member, the first member being large enough to encase both the tissue-contact end and the suture-contact end of the surgical needle-type device, the first member and the second member each having an inner surface;
    (c) means for retaining the first member to the second member, the retaining means having an engaged position and a disengaged position, both the tissue-contact end and the suture-contact end of the surgical needle-type being securely encaseable between the first member and the second member when the retaining means is in the engaged position; and
    (d) an elongated recess disposed about the perimeter of the inner surface of the second member forming part of the retaining means.

7. The needle guard apparatus of claim 6, wherein the first and the second member are sized and shaped to retain one surgical needle.

8. The needle guard apparatus of claim 7, wherein the retaining means may be readily disengaged, enabling the needle guard apparatus to package the surgical needle-type device prior to use.

9. The needle guard apparatus of claim 6 wherein the first member has a recessed portion disposed upon inner surface thereof, and the second member has a protruding portion disposed upon the inner surface thereof, the protruding portion snap-fitting into the recessed portion when the retaining means is in the engaged position.

10. The needle guard apparatus of claim 6, wherein the first member and the second member each have a plurality of mating corrugated grooves disposed therein for the secure retention of the suture.

11. The needle guard apparatus of claim 6, wherein the first and second members for an snap-fit engagement when the retaining means is in the engaged position.

12. The needle guard apparatus of claim 6, wherein a first protruding member is disposed on the inner surface of the first member, and a second protruding member is disposed on the inner surface of the second member, each protruding member having a generally cylindrical shape, the protruding members defining the retaining means.

13. A needle-guard apparatus to engage a surgical-needle device, the surgical needle device having a tissue contact end and a suture-contact end, the needle-guard apparatus comprising:
    (a) a first member and a second member being large enough to encase the surgical needle-type each having an inner surface, a first protruding element being disposed on the inner surface of the first member, a second protruding element being disposed on the inner surface of the second member;
(b) means for retaining the first member to the second member, the retaining means having an engaged position and a disengaged position, the first protruding element forming a snap-fit engagement with the second protruding element when the retaining means is in the engaged position, the surgical needle-type device being securely encaseable between the first member and the second member when the retaining means is in the engaged position; and
(c) the first protruding element mates into the second protruding element, and is permanently retained therein when the retaining means is engaged.

14. A suture-extender apparatus for the secure retention of a needle-type device, the needle-type device having two ends, one end of the needle-type device being affixable to a suture, the apparatus comprising:
(a) a first member and a second member, the first member being large enough to encase both ends of the needle-type device, the first member and the second member each having an inner surface, the first and second member being sized and shaped to retain therewithin a surgical needle; and
(b) means for retaining the second member to the first member when the needle-type device is disposed therebetween, the retaining means comprising a protruding portion which extends continuously about a major portion of the inner surfaces of the second member, the retaining means having an engaged position and a disengaged position, both ends of the needle-type device being securely encaseable between the first member and the second member when the retaining means is the engaged position; and
wherein the suture extender readily fits into a hand of a physician, enabling the physician to complete a surgical operation without exposure to puncture from the needle-type device.

* * * * *